United States Patent
Dąbrowska-Maś et al.

(10) Patent No.: US 10,941,097 B2
(45) Date of Patent: Mar. 9, 2021

(54) METHODS FOR MANUFACTURING PHENOXYETHANOL

(71) Applicant: Bausch Health Ireland Limited, Dublin (IE)

(72) Inventors: Elżbieta Dąbrowska-Maś, Rzeszów (PL); Wojciech Raś, Rzeszów (PL); Bartłomiej Ataman, Rzeszów (PL); Kazimierz Smolak, Rzeszów (PL); Adam Pszeniczny, Rzeszów (PL)

(73) Assignee: Bausch Health Ireland Limited, Dublin (IE)

( * ) Notice: Subject to any disclaimer, the term of this patent is extended or adjusted under 35 U.S.C. 154(b) by 0 days.

(21) Appl. No.: 16/604,244

(22) PCT Filed: Apr. 13, 2018

(86) PCT No.: PCT/EP2018/059564
§ 371 (c)(1),
(2) Date: Oct. 10, 2019

(87) PCT Pub. No.: WO2018/189385
PCT Pub. Date: Oct. 18, 2018

(65) Prior Publication Data
US 2020/0199057 A1    Jun. 25, 2020

Related U.S. Application Data

(60) Provisional application No. 62/485,656, filed on Apr. 14, 2017.

(51) Int. Cl.
C07C 41/14     (2006.01)
C07C 41/42     (2006.01)
C07C 43/23     (2006.01)

(52) U.S. Cl.
CPC .............. *C07C 41/14* (2013.01); *C07C 41/42* (2013.01); *C07C 43/23* (2013.01)

(58) Field of Classification Search
CPC .................. C07C 41/14; C07C 41/42
See application file for complete search history.

(56) References Cited

FOREIGN PATENT DOCUMENTS

CN    105693666    6/2016
FR    2549828      2/1985

OTHER PUBLICATIONS

Zhongping Hu et al: "Synthesis and antibacterial activity of 3-benzylamide derivatives as FtsZ inhibitors", Bioorganic & Medicinal Chemistry Letters, vol. 27, No. 8, Feb. 17, 2017, pp. 1854-1858, XP055483053, Amsterdam, NL, ISSN: 0960-894X, DOI: 10.1016/j.bmcl.2017.02.032.
Zhongping Hu et al: "Supplementary material—Synthesis and antibacterial activity of 3-benzylamide derivatives as FtsZ inhibitors", Bioorganic & Medicinal Chemistry Letters, Feb. 17, 2017, pp. 1854-1858, XP055483065, DOI: 10.1016/j.bmcl.2017.02.032 Retrieved from: http://api.elsevier.com/content/article/PII: S0960894X1730166X?httpAccept=text/xml [retrieved on Jun. 11, 2018].
Erkin A V et al: "Aryl ethers of 4-[(2-hydroxyethyl)sulfanyl]pyrimidine derivatives: Pathways of synthesis and fungicidal activity of their salt forms", Russian Journal of General Chemistry, M A I K Nauka-Interperiodica, RU, vol. 86, No. 6, Jul. 27, 2016, pp. 1274-1281, XP036015535, ISSN: 1070-3632, DOI: 10.1134/S1070363216060098 [retrieved on Jul. 27, 2016].
Vasarhelyi, Endre et al: "Chlorophenoxyalkanols", XP002781864, Database CA [Online] Chemical Abstracts Service, Columbus, Ohio, US; retrieved from STN Database accession No. 1970:476853 abstract & HU 157 457 A (Budapesti Vegyimuvek), Jun. 6, 1970.
International Search Report and Written Opinion of PCT/EP2018/059564 of the International Searching Authority dated Jun. 22, 2018 (17 pages).
Office Action issued by the Canadian Patent Office in corresponding CA Application No. 3,054,873, dated Nov. 17, 2020 (4 pages).
Sun et al., "Study on synthesis of glycol phenyl ether by phase transfer catalyst", (Article in Chinese) Jingxi Shiyou Huagong Jinzhan 9(11), pp. 24-27, 2008, ISSN: 1009-8348.

*Primary Examiner* — Sikarl A Witherspoon
(74) *Attorney, Agent, or Firm* — Andrew J. Anderson, Esq.; Harter Secrest & Emery LLP

(57) ABSTRACT

Methods for manufacturing phenoxyethanol from a reaction of a phenolate with a monohalohydrin. The phenolate is reacted with the monohalohydrin at a reaction temperature that is less than or equal to a boiling point of a reaction mixture to produce products that include the phenoxyethanol.

17 Claims, 4 Drawing Sheets

| m/z | Fragment |
|---|---|
| 138 | $[M]^+$ |
| 121 | $(M^+ - OH)$ |
| 107 | $(M^+ - HO - CH_2)$ |
| 94 | $(M^+ - CH_2 - CH - OH)$ |
| 77 | $(M^+ - HO - CH_2 - CH_2 - O)$ |

¹H-NMR Spectrum of Phenoxyethanol
Made by the method of FIG. 1

| No. | Group | Chemical shift, δ (ppm) | Signal | Integration |
|---|---|---|---|---|
| 1. | H-7 + $H_2O$ | 2.139 | singlet | 1.13 H |
| 2. | H-1 | 3.945. 3.953. 3.963 | triplet | 2.05 H |
| 3. | H-2 | 4.068. 4.078. 4.086 | triplet | 2.06 H |
| 4. | H-4 | 6.910. 6.912. 6.927. 6.929 | doublet of doublets | 2.00 H |
| 5. | H-6 | 6.952. 6.967. 6.982 | triplet | 1.00 H |
| 6. | solvent | 7.250 | singlet | |
| 7. | H-5 | 7.273. 7.277. 7.288. 7.290. 7.301. 7.305 | doublet of triplets | 2.00 H |

METHODS FOR MANUFACTURING PHENOXYETHANOL

CROSS-REFERENCE TO RELATED TO APPLICATION

This application claims the benefit of U.S. Provisional Application No. 62/485,656, filed Apr. 14, 2017, the contents of which are incorporated herein by reference in their entirety.

TECHNICAL FIELD

The present application relates to methods for manufacturing phenoxyethanol from a reaction of a phenolate with a monohalohydrin. In particular, the present application relates to methods for manufacturing phenoxyethanol having high purity. More particularly, the present application relates to methods for manufacturing pharmaceutical-grade phenoxyethanol.

BACKGROUND

Phenoxyethanol (PE, CAS 122-99-6) is an alcohol and aromatic ether, known as 2-phenoxyethanol, 2-phenoxy-1-ethanol, or ethylene glycol monophenyl ether. Phenoxyethanol is widely used as a solvent and/or an intermediate in organic synthesis, and this compound also shows moderate antibacterial and antifungal properties. Therefore, phenoxyethanol is used as a preservative in cosmetics and as an active substance in medicinal products.

Phenoxyethanol may be produced by reacting phenol and ethylene oxide in an alkaline environment. Sodium hydroxide, ammonia, urea, amines, sodium and lithium phenolates, and/or alkaline resins may be used as alkaline catalysts. Disadvantages of this approach include the presence of gaseous ethylene oxide, which requires the reaction to be run in an autoclave. Another disadvantage of this method is that the ethylene oxide must be added in a manner that increases the selectivity toward a mono-derivative, which is an expected product, relative to condensation products, e.g., to 2-(2-phenoxyethoxy)ethanol. At the same time, in order to obtain a product that can be acceptable in pharmaceutical and cosmetic products, the reaction should be performed so that 4%-8% of the phenoxyethanol further reacts to produce a condensation product, 2-(2-phenoxyethoxy)ethanol (di-ethoxylane). Further reacting the phenoxyethanol in such a manner reduces the quantity of unreacted phenol, which is otherwise difficult to remove from the final product and is disfavored in pharmaceutical and cosmetic products. Taken together, all of this means that the process should be tightly controlled, e.g., through an in-process control of the reaction yield or impurities content. As a result, this process may be less economical.

Also, high-purity phenoxyethanol can be obtained by reaction of ethylene oxide and phenol in the presence of alkaline catalyst, without solvent addition, and where the catalyst is partly neutralized.

In other processes, phenoxyethanol may be produced from a reaction of monochlorohydrins (e.g., 2-chloroethanol) with a substituted or unsubstituted phenol, where trimethylamine is used as a catalyst. However, such a method can be considered disadvantageous because of low reaction yields.

Another method for producing phenoxyethanol includes mixing 2-chloroethanol and 30% sodium hydroxide solution with phenol at the temperature of 100° C. to 110° C. The process yield is 98%, although industrial application of the process has not been described.

A "green chemistry" approach to phenoxyethanol production is to react a substituted or unsubstituted phenol and ethylene carbonate in the presence of alkaline catalysts. The alkaline catalysts may be alkaline carbonates, lithium hydride, tetraethylammonium iodide, and/or iodides and/or phosphates of alkali metals. This method may be disadvantageous because of the presence of undesired condensation by-products and the difficulty of catalyst recovery from the reaction mixture. A heterogeneous alkaline catalyst, such as Na-Mordenite, which can be readily separated from the reaction mixture, may be used with this method. One disadvantage of this modified process is that the process must be run at high temperatures, in the region of 210° C. to 250° C., because at lower temperatures, e.g., 150° C., only about 10% reaction can be reached over 35 hours. Therefore, a disadvantage of this process, if implemented commercially, is the necessity to employ less economic methods to maintain such high temperatures over an extended period of time.

A drawback of most of the above processes of phenoxyethanol production is that phenoxyethanol (boiling point of about 245° C.) is purified by distillation. However, distillation is ineffective for removal of unreacted phenol, which sublimes under distillation conditions and passes into the distillate.

Usually, cosmetic grade phenoxyethanol is at least 98% pure, and phenol impurities do not exceed 1%.

Phenoxyethanol obtained by conventional methods may not be acceptable for use in pharmaceutical applications because the resulting product is not phenol-free. For phenoxyethanol to have an acceptable phenol content for pharmaceutical applications, the product must comply with the requirements of European Union legislation (depending on the amount of active substance to be administered daily, as described in European Pharmacopoeia Monograph 07/2016: 0781) or any generally equivalent U.S. standard. The European Pharmacopoeia mandates that when phenoxyethanol is used as an active substance, the phenol content must not be more than 0.10% w/w. For non-specified impurities, including polymerization products, the European limit for an acceptable content of one such single impurity in a pharmaceutical product is also typically not more than 0.10% w/w (depending on the amount of active substance to be administered daily).

SUMMARY

In one embodiment, methods for manufacturing phenoxyethanol include reacting phenolate with a monohalohydrin at a reaction temperature no greater than (i.e., is less than or equal to) a boiling point of the reaction mixture to produce products. These products include the phenoxyethanol.

The monohalohydrin may be a 2-haloethanol. The 2-haloethanol may include a halogen selected from the group consisting of chloro-, bromo-, iodo-, and fluoro-. The phenolate may be an alkali metal phenolate hydrate, for example a sodium phenolate trihydrate. In some embodiments, a catalyst is not present in the reaction. In one embodiment, the reaction temperature is about 65° C. to about 75° C. In the same or a different embodiment, the mixture of the phenolate and monohalohydrin is aqueous. In the same or a different embodiment, the monohalohydrin may be added to the phenoxyethanol dropwise for a period of time.

The methods may include cooling the reaction, extracting the products from the cooled reaction mixture by addition of an organic solvent immiscible in water to form an organic phase, washing the organic phase with an alkaline aqueous solution, and, subsequent to washing the organic phase, fractionally distilling phenoxyethanol from the washed organic phase. This phenoxyethanol may have no more than (i.e., less than or equal to) 0.10% w/w of phenol and less than or equal to 0.10% w/w of each of one or more unspecified impurities, including the unspecified impurity of 2-(2-phenoxyethoxy)ethanol. In one embodiment, the organic solvent may comprise methylene chloride. In the same or a different embodiment, the alkaline aqueous solution may comprise a sodium hydroxide solution. In the same or a different embodiment, fractionally distilling phenoxyethanol from the washed organic phase may include heating to a distilling temperature of about 95° C. to about 120° C., which may be performed while under vacuum or at atmospheric pressure.

BRIEF DESCRIPTION OF THE DRAWINGS

The claimed subject matter is described with reference to the accompanying drawings. A brief description of each figure is provided below. Elements with the same reference number in each figure indicate identical or functionally similar elements.

DETAILED DESCRIPTION

Figure 1:
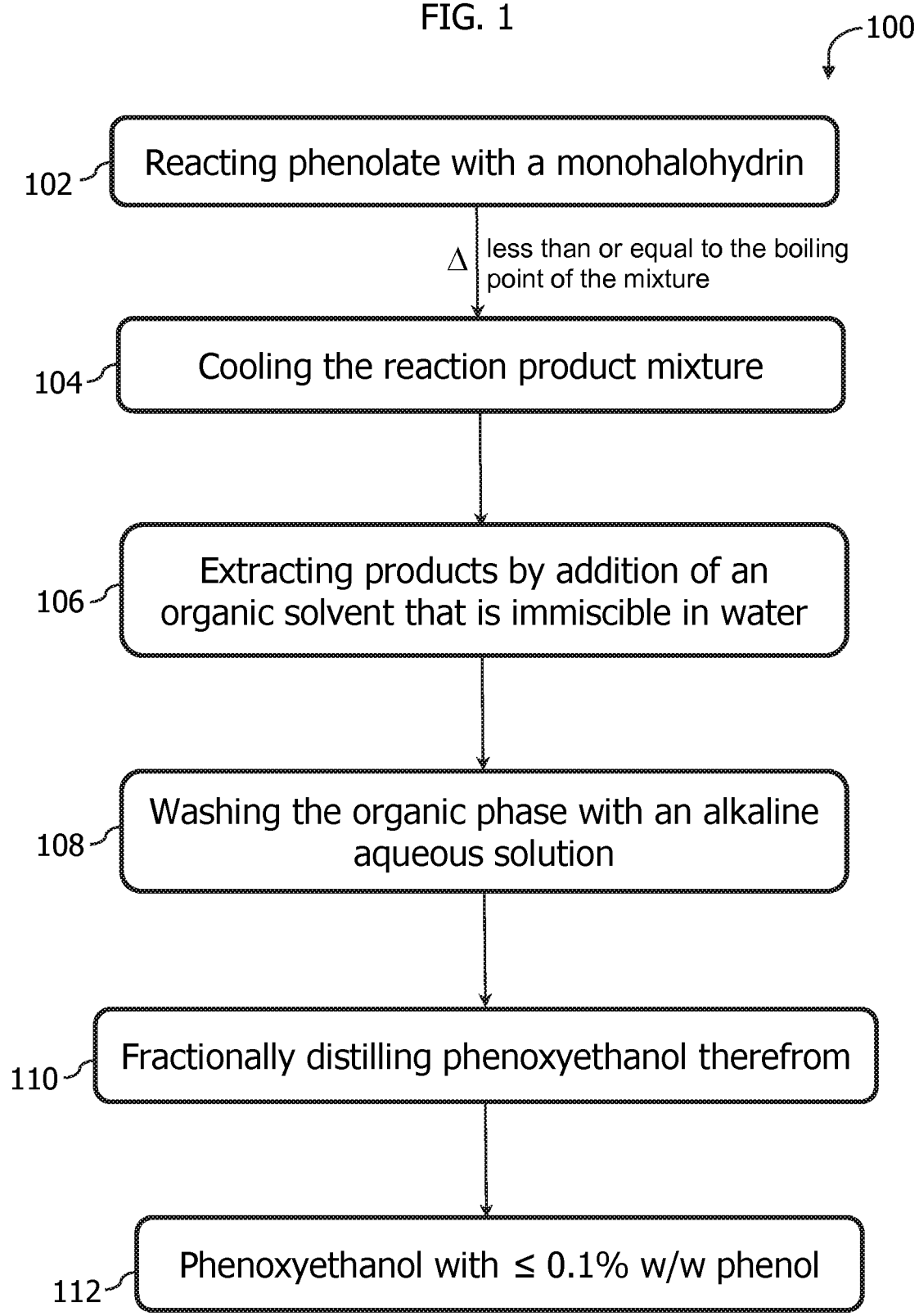
FIG. 1 is a flow chart of a method for manufacturing phenoxyethanol.

Referring to FIG. 1 and reaction scheme (I) below, methods 100 for manufacturing phenoxyethanol are disclosed that result in a yield of at least 75% of the theoretical yield and that have less than or equal to 0.10% w/w of phenol as an impurity and less than or equal to 0.01% w/w of each of one or more unspecified impurities present. In certain embodiments, the reaction has a yield of 80% to 85% of the theoretical yield.

The methods include reacting 102 phenolate (Formula 1) with a monohalohydrin (Formula 2). In one embodiment, the phenolate and monohalohydrin are in aqueous solutions. The reaction temperature is less than or equal to a boiling point of the reaction mixture. Thus, a reaction product mixture is formed, and this reaction product mixture includes phenoxyethanol (Formula 3).

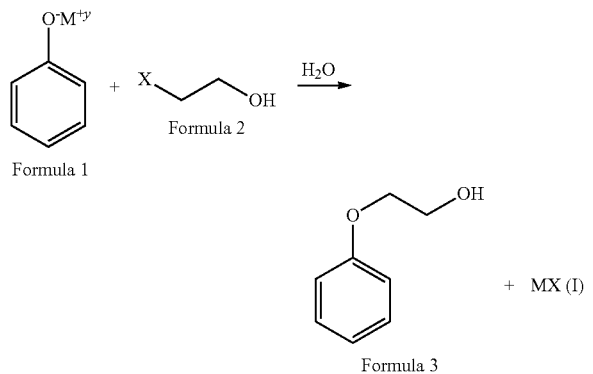

$M^{+y}$ may be an alkali metal, an alkaline earth metal, or a transition metal, wherein y is 1, 2, or 3. When y is 1, as in the reaction scheme (I) set forth above, one phenolate may be present to balance the charge of the metal. When y is 2 or y is 3, two phenolates or three phenolates, respectively, may be present to balance the charge of the metal. Accordingly, the phenolate may be an alkali metal ($M^+$) phenolate, an alkaline earth metal ($M^{2+}$) phenolate, or a transition metal ($M^{3+}$) phenolate. Each of these species may be hydrated. In one embodiment, the phenolate is a sodium phenolate trihydrate. In another embodiment, the phenolate is an aluminum phenolate.

The method further includes cooling 104 the reaction product mixture, extracting products 106 from the cooled reaction product mixture by addition of an organic solvent immiscible in water to form an organic phase, washing 108 the organic phase with an alkaline aqueous solution, and optionally, subsequent to washing the organic phase, fractionally distilling 110 phenoxyethanol from the washed organic phase. Cooling 104 may be to about room temperature. The phenoxyethanol 112 may have less than or equal to 0.10% w/w phenol present, which may make this product suitable for cosmetic and/or pharmaceutical applications.

In some embodiments, a catalyst is not present in the reaction at any step of the method. In the same or a different embodiment, the reaction temperature is a moderate temperature, being less than or equal to the boiling point of the reaction mixture. In one embodiment, the reaction temperature may be in the range of about 65° C. to about 75° C. and is maintained for 10 minutes to 24 hours. "About" as used herein for temperature values means within 5% thereof. In one embodiment, the reaction time is from 0.5 hour to 24 hours, or 1 hour to 24 hours, or 1 hour to 20 hours, or 1 hour to 15 hours, or 1 hour to 10 hours, or 1 hour to 7 hours, or 1 hour to 6 hours, or 1 hour to 5 hours, or 1 hour to 3 hours, or 0.5 hour to 5 hours, or 0.5 hour to 3 hours.

In some embodiments, the monohalohydrin is a 2-haloethanol. The 2-haloethanol may include a halogen selected from the group consisting of chloro-, bromo-, iodo-, and fluoro-(X, in reaction scheme (I)).

Suitable organic solvents include, but are not limited to, hydrocarbons (e.g., benzene, toluene, xylene, pentane, hexane, heptane, cyclohexane), esters (e.g., ethyl acetate, butyl acetate), ethers (e.g., di-ethyl ether, methyl-t-butyl ether), chlorinated hydrocarbons (e.g., carbon tetrachloride, chloroform, 1,2-dichloroethanol, methylene chloride, trichloroethylene), alcohols (e.g., n-butanol), and combinations thereof. In one embodiment, the organic solvent may be or may include methylene chloride.

The alkaline aqueous solution may be, but is not limited to, a solution of an alkali metal hydroxide (e.g., NaOH, KOH, LiOH), an alkaline earth metal hydroxide (e.g., Be(OH)$_2$), an inorganic salt of a weak acid (e.g., carbonates), an organic salt of a weak acid (e.g., fumarate, oxalate, maleate), or combinations thereof. In one embodiment, the alkaline aqueous solution may be or may include sodium hydroxide.

The method for reacting the phenoxyethanol with the monohalohydrin may include adding the monohalohydrin to the phenoxyethanol as a plurality of discrete portions over a period of time; for example from 1 minute to 10 hours. In embodiments of the present invention, this time can be from 1 minute to 8 hours, from 1 minute to 7 hours, from 1 minute to 6 hours, from 1 minute to 5 hours, from 1 minute to 4 hours, from 1 minute to 3 hours, from 1 minute to 2 hours, from 1 minute to 1 hour, from 1 minute to 30 minutes, from 10 minutes to 8 hours, from 10 minutes to 7 hours, from 10 minutes to 6 hours, from 10 minutes to 5 hours, from 10 minutes to 4 hours, from 10 minutes to 3 hours, from 10 minutes to 2 hours, from 10 minutes to 1 hour, or from 10 minutes to 30 minutes. In one embodiment, the discrete portions are drops added dropwise, for example from a burette, dropper, pipette, or other similar apparatus. The discrete portions can be of equal amounts relative to each other and may be added sequentially over a time period, as disclosed above, until the monohalohydrin is added in its entirety. The drops may be added every 5 seconds, every 10 seconds, every 30 seconds, every one minute, every 5 minutes, or every 10 minutes. In another embodiment, rather than drops, the additions may be in larger volume aliquots, as recognized by a person of ordinary skill in the art. In another embodiment, the monohalohydrin can be added into the medium containing phenoxyethanol at a substantially constant rate over a period of time, such as the time periods disclosed above.

After adding the monohalohydrin, the reaction may be maintained at the reaction temperature for a time period of 0.5 hour to 24 hours, or 1 hour to 24 hours, or 1 hour to 20 hours, or 1 hour to 15 hours, or 1 hour to 10 hours, or 1 hour to 7 hours, or 1 hour to 6 hours, or 1 hour to 5 hours, or 1 hour to 3 hours, or 0.5 hour to 5 hours, or 0.5 hour to 3 hours. In one embodiment, the reaction time may be 6 hours. In another embodiment, the reaction time may be 7 hours.

In one embodiment, fractionally distilling the phenoxyethanol from the washed organic phase may be performed at a distilling temperature of about 95° C. to about 120° C. under decreased pressure or within the boiling temperature range at atmospheric pressure. In this way, an impurity formed during the reaction, 2-(2-phenoxyethoxy)ethanol (Formula 4), may be removed.

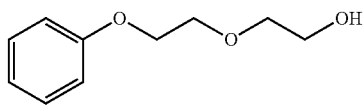

Formula 4

In one embodiment, the final phenoxyethanol product may be substantially free of phenol and 2-(2-phenoxyethoxy)ethanol. Each of free phenol and 2-(2-phenoxyethoxy)ethanol may be present at less than or equal to 0.10% w/w, which meets the European Pharmacopoeia requirements. As such, the phenoxyethanol produced by the methods disclosed herein may be acceptable for use in pharmaceutical products. Besides this advantage, the methods do not require special equipment or conditions and, therefore, may be easily implemented on a production scale.

WORKING EXAMPLES

Example 1

85.8 g of water were added to 33.0 g of sodium phenolate trihydrate, and the mixture was stirred until dissolved. A solution of 15.6 g of 2-chloroethanol in 12.9 g water was prepared separately. The aqueous solution of sodium phenolate trihydrate was heated to 70° C. and the aqueous solution of 2-chloroethanol was added to the solution dropwise continuously during a 1 hour time period while maintaining the temperature at 70° C. The reaction was performed for 5 hours at the temperature of 70° C. After the reaction mixture was allowed to cool to room temperature, the product was extracted with methylene chloride to form an organic phase. The organic phase was washed twice with a 5% aqueous solution of sodium hydroxide, and the solvent was distilled off. Phenoxyethanol was fractionally distilled under decreased pressure in an apparatus comprising a packed column, where a fraction with a boiling point within the range of 95° C. to 120° C. was collected. 22.0 g of phenoxyethanol were obtained, which is 82% w/w of the theoretical yield.

Figure 2:
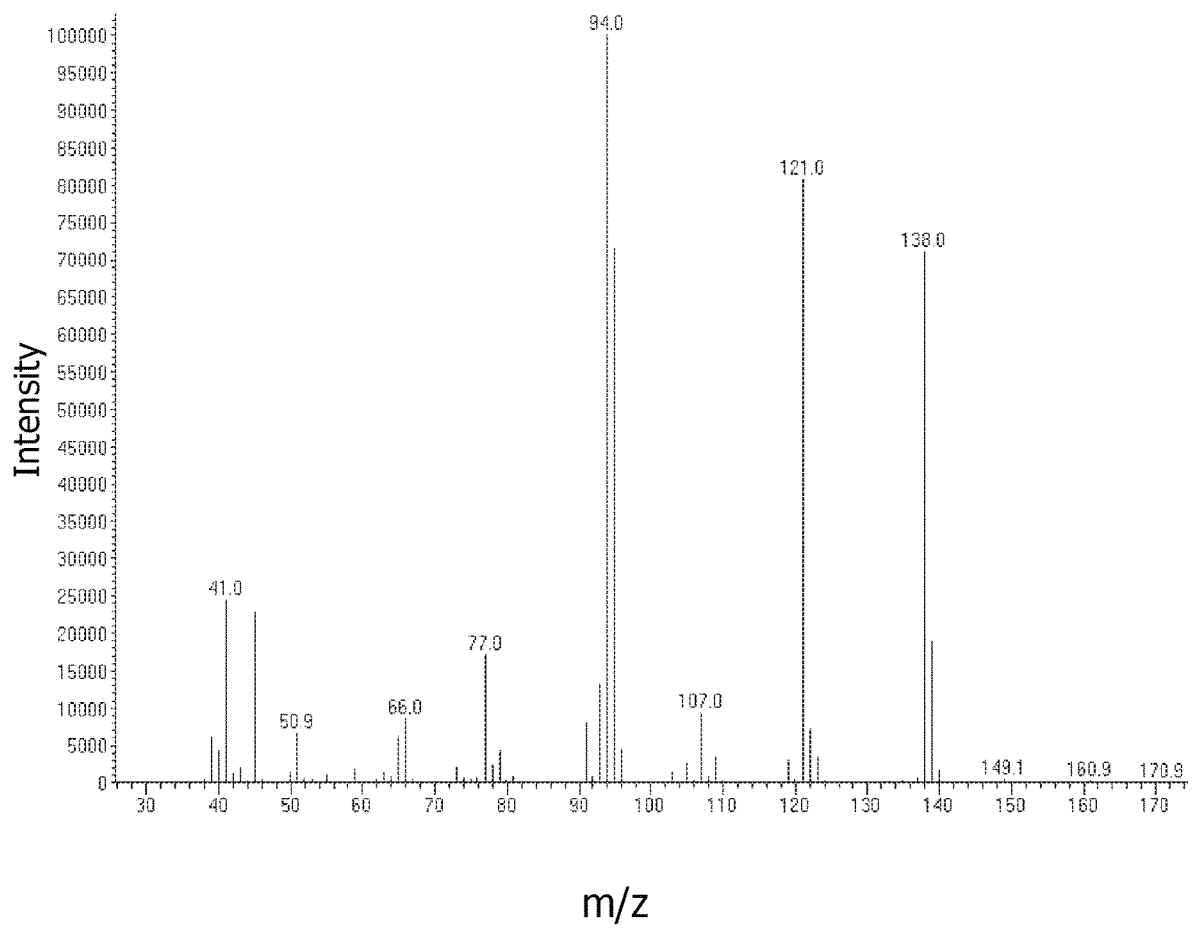
FIG. 2 is a mass spectrometry (MS) Spectrum of phenoxyethanol made by the method of FIG. 1.
Figure 3:
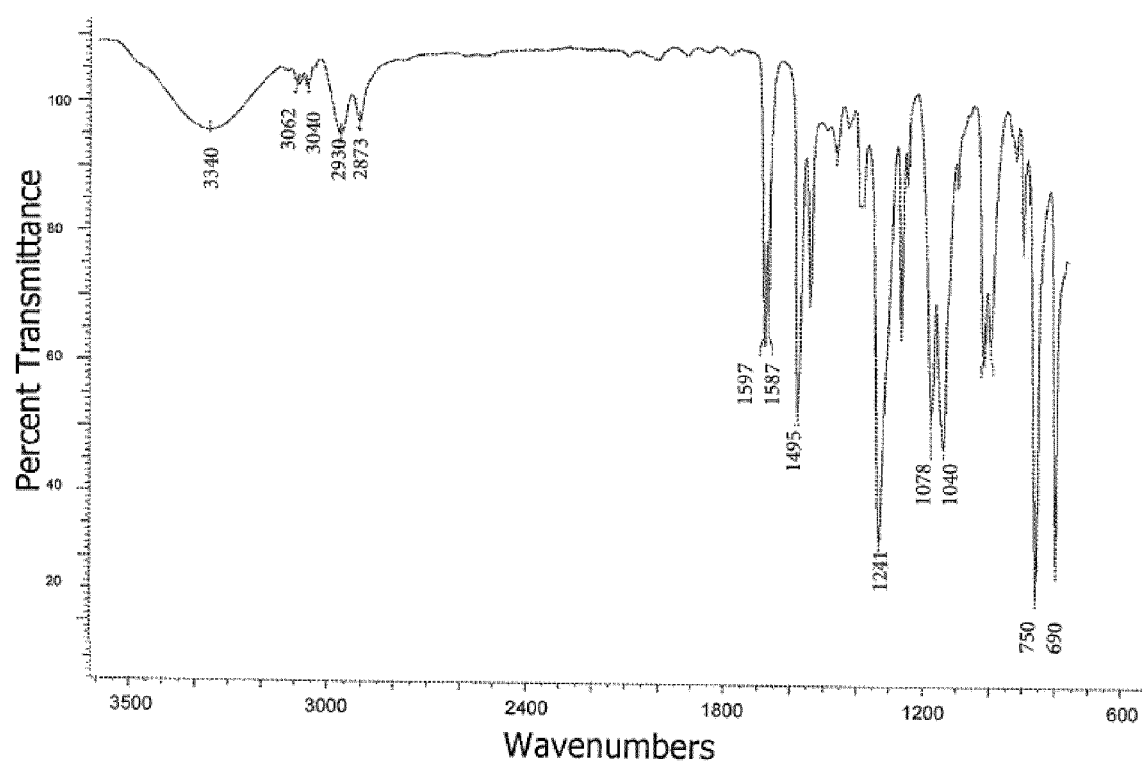
FIG. 3 is an infrared (IR) Spectrum of phenoxyethanol made by the method of FIG. 1.
Figure 4:
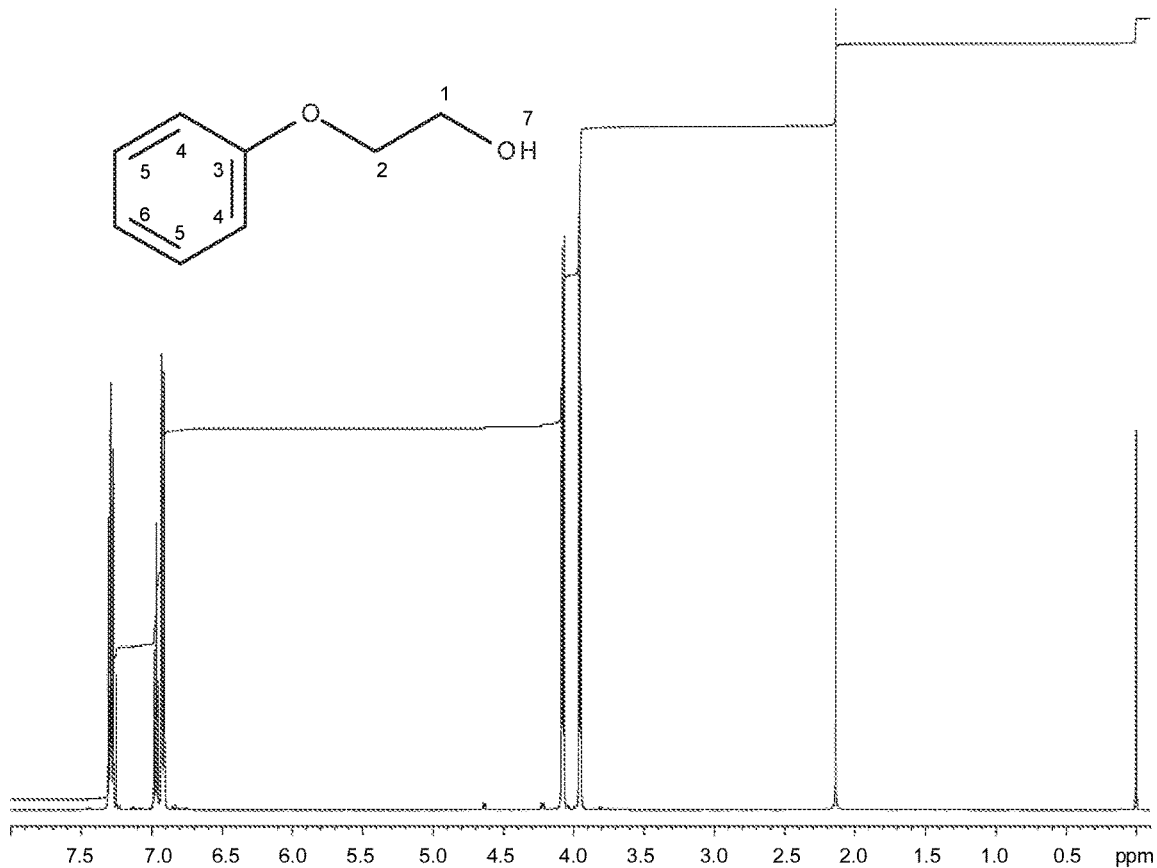
FIG. 4 is an $^1$H nuclear magnetic resonance ($^1$H-NMR) Spectrum of phenoxyethanol made by the method of FIG. 1.

The phenoxyethanol was analyzed by mass spectrum (MS) analysis, infrared (IR) spectroscopy analysis, and $^1$H-NMR spectroscopy analysis, as shown in FIGS. 2-4. The MS spectrum of FIG. 2 evidences C—68.78% (theoretic 69.52); H—7.39% (theoretic 7.31%). The IR spectrum evidences O—H at 3340 cm$^{-1}$, C—H aromatic at 3062 cm$^{-1}$ and 3040 cm$^{-1}$, CH$_2$ at 2930 cm$^{-1}$ and 2873 cm$^{-1}$, C=C at 1597 cm$^{-1}$, 1587 cm$^{-1}$, and 1495 cm$^{-1}$, aryl-O—C at 1241 cm$^{-1}$ and 1040 cm$^{-1}$, CH$_2$—OH at 1078 cm$^{-1}$, C—H aromatic at 750 cm$^{-1}$, and C=C aromatic at 690 cm$^{-1}$.

The $^1$H-NMR spectrum evidences that the concentration of phenol impurity is below 0.10% w/w and that of 2-(2-phenoxyethoxy)ethanol is below 0.10% w/w.

Example 2

44.3 g of water were added to 17.0 g of sodium phenolate trihydrate, and the solution was heated to 70° C. 12.5 g of 2-bromoethanol were added to the solution dropwise continuously during a 1 hour time period. The reaction was performed for 6 hours at the temperature of 70° C. After the reaction mixture cooled to room temperature, the product was extracted with methylene chloride to form an organic phase. The organic phase was washed twice with a 5% aqueous solution of sodium hydroxide, and the solvent was distilled off Phenoxyethanol was fractionally distilled under decreased pressure in an apparatus comprising a packed column, where a fraction with a boiling point within the range of 95° C. to 120° C. was collected. 11.0 g of phenoxyethanol were obtained, which is 80% w/w of the theoretical yield.

Example 3

44.3 g of water were added to 17.0 g of sodium phenolate trihydrate, and the solution was heated to 70° C. 6.4 g of 2-fluoroethanol were added to the solution dropwise continuously during a 1 hour time period. The reaction was performed for 5 hours at the temperature of 70° C. After the reaction mixture cooled to room temperature, the product was extracted with methylene chloride to form an organic phase. The organic phase was washed twice with a 5% aqueous solution of sodium hydroxide, and the solvent was distilled off. Phenoxyethanol was fractionally distilled under decreased pressure in an apparatus comprising a packed column, where a fraction with a boiling point within the range of 95° C. to 120° C. was collected. 11.2 g of phenoxyethanol were obtained, which is 81% w/w of the theoretical yield.

Example 4

44.3 g of water were added to 17.0 g of sodium phenolate trihydrate, and the solution was heated to 70° C. 17.2 g of 2-iodoethanol were added to the solution dropwise continuously during a 1 hour time period. The reaction was performed for 7 hours at the temperature of 70° C. After the reaction mixture cooled to room temperature, the product was extracted with methylene chloride to form an organic phase. The organic phase was washed twice with a 5% aqueous solution of sodium hydroxide, and the solvent was distilled off Phenoxyethanol was fractionally distilled under decreased pressure in an apparatus comprising a packed column, where a fraction with a boiling point within the range of 95° C. to 120° C. was collected. 10.9 g of phenoxyethanol were obtained, which is 79% w/w of the theoretical yield.

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

The invention claimed is:

1. A method for manufacturing phenoxyethanol, the method comprising:
    reacting phenolate with a monohalohydrin at a reaction temperature that is less than or equal to a boiling point of a reaction mixture, wherein a catalyst is not present, to produce products that include the phenoxyethanol.

2. The method of claim 1, further comprising:
    cooling the reaction mixture;
    extracting the products from the cooled reaction mixture by addition of an organic solvent immiscible in water to form an organic phase;
    washing the organic phase with an alkaline aqueous solution; and
    subsequent to washing the organic phase, fractionally distilling the phenoxyethanol from the washed organic phase.

3. The method of claim 2, wherein the organic solvent comprises methylene chloride.

4. The method of claim 2, wherein the alkaline aqueous solution comprises a sodium hydroxide solution.

5. The method of claim 2, wherein fractionally distilling the phenoxyethanol from the washed organic phase further comprises:
    heating to a distilling temperature of about 95° C. to about 120° C.

6. The method of claim 5, wherein fractionally distilling the phenoxyethanol from the washed organic phase further comprises:
    heating while under decreased pressure.

7. The method of claim 5, wherein fractionally distilling the phenoxyethanol from the washed organic phase further comprises:
    heating to the distilling temperature while at atmospheric pressure.

8. The method of claim 1, wherein the reaction mixture of the phenolate and the monohalohydrin is aqueous.

9. The method of claim 1, wherein the phenolate is an alkali metal phenolate hydrate.

10. The method of claim 9, wherein the phenolate is a sodium phenolate trihydrate.

11. The method of claim 1, wherein the monohalohydrin is a 2-haloethanol.

12. The method of claim 11, wherein the 2-haloethanol comprises a halogen selected from the group consisting of chloro-, bromo-, iodo-, and fluoro-.

13. The method of claim 1, wherein the reaction temperature is about 65° C. to about 75° C.

14. The method of claim 1, wherein reacting the phenolate with the monohalohydrin comprises:
    adding the monohalohydrin to the phenolate dropwise for a period of time.

15. The method of claim 1, wherein the phenoxyethanol includes less than or equal to 0.10% w/w of phenol.

16. The method of claim 15, wherein the phenoxyethanol includes less than or equal to 0.10% w/w of each of one or more unspecified impurities.

17. The method of claim 16, wherein one of the one or more unspecified impurities is 2-(2-phenoxyethoxy)ethanol.

* * * * *